US005674749A

United States Patent [19]

Chen et al.

[11] Patent Number: 5,674,749

[45] Date of Patent: Oct. 7, 1997

[54] MONOCLONAL ANTIBODIES WHICH BIND TO TUMOR REJECTION ANTIGEN PRECURSOR MELAN-A, AND USES THEREOF

[75] Inventors: Yao-tseng Chen; Elisabeth Stockert; Achim Jungbluth; Lloyd J. Old, all of New York, N.Y.

[73] Assignees: Ludwig Institute For Cancer Research; Memorial Sloan Kettering Cancer Center; Cornell Research Foundation, Inc., all of New York, N.Y.

[21] Appl. No.: 622,067

[22] Filed: Mar. 26, 1996

[51] Int. Cl.$^6$ .............................. C12N 5/12; C07K 16/00; C12P 21/08

[52] U.S. Cl. ....................... 435/344.1; 530/388.1; 530/388.85

[58] Field of Search .................... 530/388.1, 388.85; 435/240.27, 344.1

[56] References Cited

FOREIGN PATENT DOCUMENTS

WO9421126   9/1994   WIPO.
9529193    11/1995   WIPO.

OTHER PUBLICATIONS

Coulie et al., "A New Gene Coding For A differentiation Antigen–Recognized By Autologous Cytolytic T Lymphocytes On HLA–A2 Melanomas," J. Exp. Med. 180: 35–42 (Jul. 1994).

Kawakami et al., "Indentification of the Immunodominant Peptides–of the Mart–1 Human Melanoma Antigen Recognized by the Majority of HLA–A2 Restricted Tumor Infiltrating Lymphocytes", J. Exp. Med. 180: 347–352 (Jul. 1994).

Chen et al., "Identification of the MAGE–1 Gene Product By –Monoclonal And Polyclonal Antibodies". Proc. Natl. Acad. Sci. USA 91: 1004–1008 (Feb. 1994).

Primary Examiner—Anthony C. Caputa
Assistant Examiner—Mark Navarro
Attorney, Agent, or Firm—Felfe & Lynch

[57] ABSTRACT

The invention relates to monoclonal antibodies which specifically bind to the tumor rejection antigen precursor molecule Melan-A, hybridomas which produce these monoclonal antibodies, and their use. Also described is a recombinant form of Melan-A and immunogenic compositions containing the molecules, and an adjuvant.

2 Claims, No Drawings

MONOCLONAL ANTIBODIES WHICH BIND TO TUMOR REJECTION ANTIGEN PRECURSOR MELAN-A, AND USES THEREOF

FIELD OF THE INVENTION

This invention relates in general to the field of immunology. More specifically, it refers to monoclonal antibodies and antisera directed against Melan-A, a tumor rejection antigen precursor or "TRAP", as well as their use. Of special interest is the use of these monoclonal antibodies in immunohistochemical analysis.

BACKGROUND AND PRIOR ART

The study of the recognition or lack of recognition of cancer cells by a host organism has proceeded in many different directions. Understanding of the field presumes some understanding of both basic immunology and oncology.

Early research on mouse tumors revealed that these displayed molecules which led to rejection of tumor cells when transplanted into syngeneic animals. These molecules are "recognized" by T-cells in the recipient animal, and provoke a cytolytic T-cell response with lysis of the transplanted cells. This evidence was first obtained with tumors induced in vitro by chemical carcinogens, such as methylcholanthrene. The antigens expressed by the tumors and which elicited the T-cell response were found to be different for each tumor. See Prehn, et al., J. Natl. Canc. Inst. 18:769–778 (1957); Klein et al., Cancer Res. 20: 1561–1572 (1960); Gross, Cancer Res. 3:326–333 (1943), Basombrio, Cancer Res. 30:2458–2462 (1970) for general teachings on inducing tumors with chemical carcinogens and differences in cell surface antigens. This class of antigens has come to be known as "tumor specific transplantation antigens" or "TSTAs". Following the observation of the presentation of such antigens when induced by chemical carcinogens, similar results were obtained when tumors were induced in vitro via ultraviolet radiation. See Kripke, J. Natl. Canc. Inst. 53:333–1336 (1974).

While T-cell mediated immune responses were observed for the types of tumor described supra, spontaneous tumors were thought to be generally non-immunogenic. These were therefore believed not to present antigens which provoked a response to the tumor in the tumor carrying subject. See Hewitt, et al., Brit. J. Cancer 33: 241–259 (1976).

The family of tum antigen presenting cell lines are immunogenic variants obtained by mutagenesis of mouse tumor cells or cell lines, as described by Boon et al., J. Exp. Med. 152:1184–1193 (1980), the disclosure of which is incorporated by reference. To elaborate, tum antigens are obtained by mutating tumor cells which do not generate an immune response in syngeneic mice and will form tumors (i.e., "tum$^+$" cells). When these tum$^+$ cells are mutagenized, they are rejected by syngeneic mice, and fail to form tumors (thus "tum$^-$"). See Boon et al., Proc. Natl. Acad. Sci. USA 74:272 (1977), the disclosure of which is incorporated by reference. Many tumor types have been shown to exhibit this phenomenon. See, e.g., Frost et al., Cancer Res. 43:125 (1983).

It appears that tum$^-$ variants fail to form progressive tumors because they elicit an immune rejection process. The evidence in favor of this hypothesis includes the ability of "tum$^-$" variants of tumors, i.e., those which do not normally form tumors, to do so in mice with immune systems suppressed by sublethal irradiation, Van Pel et al., Proc. Natl. Acad. Sci. USA 76:5282–5285 (1979); and the observation that intraperitoneally injected tum$^-$ cells of mastocytoma P815 multiply exponentially for 12–15 days, and then are eliminated in only a few days in the midst of an influx of lymphocytes and macrophages (Uyttenhove et al., J. Exp. Med. 152: 1175–1183 (1980)). Further evidence includes the observation that mice acquire an immune memory which permits them to resist subsequent challenge to the same tum$^-$ variant, even when immunosuppressive amounts of radiation are administered with the following challenge of cells (Boon et al., Proc. Natl. Acad. Sci. USA 74:272–275 (1977); Van Pel et al., supra; Uyttenhove et al., supra). Later research found that when spontaneous tumors were subjected to mutagenesis, immunogenic variants were produced which did generate a response. Indeed, these variants were able to elicit an immune protective response against the original tumor. See Van Pel et al., J. Exp. Med. 157:1992–2001 (1983). Thus, it has been shown that it is possible to elicit presentation of a so-called "tumor rejection antigen" in a tumor which is a target for a syngeneic rejection response. Similar results have been obtained when foreign genes have been transfected into spontaneous tumors. See Fearon et al., Cancer Res. 48:2975–1980 (1988) in this regard.

A class of antigens has been recognized which are presented on the surface of tumor cells and are recognized by cytotoxic T cells, leading to lysis. This class of antigens will be referred to as "tumor rejection antigens" or "TRAs" hereafter. TRAs may or may not elicit antibody responses. The extent to which these antigens have been studied has been via cytolytic T cell characterization studies in vitro i.e., the study of the identification of the antigen by a particular cytolytic T cell ("CTL" hereafter) subset. The subset proliferates upon recognition of the presented tumor rejection antigen, and the cells presenting the antigen are lysed. Characterization studies have identified CTL clones which specifically lyse cells expressing the antigens. Examples of this work may be found in Levy et al., Adv. Cancer Res. 24:1–59 (1977); Boon et al., J. Exp. Med. 152:1184–1193 (1980); Brunner et al., J. Immunol. 124:1627–1634 (1980); Maryanski et al., Eur. J. Immunol. 124:1627–1634 (1980); Maryanski et al., Eur. J. Immunol. 12:406–412 (1982); Palladino et al., Canc. Res. 47: 5074–5079 (1987). This type of analysis is required for other types of antigens recognized by CTLs, including major histocompatibility antigens, the male specific H-Y antigens, and a class of antigens, referred to as "tum$^-$" antigens, and discussed herein.

A tumor exemplary of the subject matter described supra is known as P815. See DePlaen et al., Proc. Natl. Acad. Sci. USA 85: 2274–2278 (1988); Szikora et al., EMBO J 9:1041–1050 (1990), and Sibille et al., J. Exp. Med. 172:35–45 (1990), the disclosures of which are incorporated by reference. The P815 tumor is a mastocytoma, induced in a DBA/2 mouse with methylcholanthrene and cultured as both an in vitro tumor and a cell line. The P815 line has generated many tum$^-$ variants following mutagenesis, including variants referred to as P91A (DePlaen, supra), 35B (Szikora, supra), and P198 (Sibille, supra). In contrast to tumor rejection antigens—and this is a key distinction—the tum$^-$ antigens are only present after the tumor cells are mutagenized. Tumor rejection antigens are present on cells of a given tumor without mutagenesis. Hence, with reference to the literature, a cell line can be tum$^+$, such as the line referred to as "P815", and can be provoked to produce tum$^-$ variants. Since the tum$^-$ phenotype differs from that of the parent cell line, one expects a difference in the DNA of tum$^-$ cell lines as compared to their tum$^+$ parental lines, and this difference can be exploited to locate the gene of interest in tum⁻ cells. As a result, it was found that genes of tum⁻ variants such as P91A, 35B and P198 differ from their normal alleles by point mutations in the coding regions of the gene. See Szikora and Sibille, supra, and Lurquin et al., Cell 58:293–303 (1989). This has proved not to be the case with the TRAs of this invention. These papers also demonstrated that peptides derived from the tum⁻ antigen are presented by the $L^d$ molecule for recognition by CTLs. P91A is presented by $L^d$, P35 by $D^d$ and P198 by $K^d$.

Prior patent applications PCT/US92/0435 and U.S. Pat. No. 5,342,774, both of which are incorporated by reference, describe inventions involving, inter alia, genes and other nucleic acid molecules which code for various TRAPs, which are in turn processed to tumor rejection antigen, or "TRAs". These TRAPs are referred to as MAGE molecules, such as MAGE-1, MAGE-2, etc.

The genes are useful as a source for the isolated and purified tumor rejection antigen precursor and the TRAs themselves, any of which can be used as an agent for treating the cancer for which an antigen is a "marker", as well as in various diagnostic and surveillance approaches to oncology, discussed infra. It is known, for example, that tum⁻ cells can be used to generate CTLs which lyse cells presenting different tum⁻ antigens as well as tum⁺ cells. See, e.g., Maryanski et al., Eur. J. Immunol 12:401 (1982); and Van den Eynde et al., Modern Trends in Leukemia IX (June 1990), the disclosures of which are incorporated by reference. The tumor rejection antigen precursor may be expressed in cells transfected by the gene, and then used to generate an immune response against a tumor of interest.

In the parallel case of human neoplasms, it has been observed that autologous mixed lymphocyte-tumor cell cultures ("MLTC" hereafter) frequently generate responder lymphocytes which lyse autologous tumor cells and do not lyse natural killer targets, autologous EBV-transformed B cells, or autologous fibroblasts (see Anichini et al., Immunol. Today 8:385–389 (1987)). This response has been particularly well studied for melanomas, and MLTC have been carried out either with peripheral blood cells or with tumor infiltrating lymphocytes. Examples of the literature in this area include Knuth et al., Proc. Natl. Acad. Sci. USA 86:2804–2802 (1984); Mukherji et al., J. Exp. Med. 158:240 (1983); Hérin et all, Int. J. Canc. 39:390–396 (1987); Topalian et al, J. Clin. Oncol 6:839–853 (1988). Stable cytotoxic T cell clones ("CTLs" hereafter) have been derived from MLTC responder cells, and these clones are specific for the tumor cells. See Mukherji et al., supra, Hérin et al., supra, Knuth et al., supra. The antigens recognized on tumor cells by these autologous CTLs do not appear to represent a cultural artifact, since they are found on tumor cells in vivo. Topalian et al., supra; Degiovanni et al., Eur. J. Immunol. 20:1865–1868 (1990). These observations, coupled with the techniques used herein to isolate the genes for specific murine tumor rejection antigen precursors, have led to the isolation of nucleic acid sequences coding for tumor rejection antigen precursors of TRAs presented on human tumors. It is now possible to isolate the nucleic acid sequences which code for tumor rejection antigen precursors, including, but not being limited to those most characteristic of a particular tumor, with ramifications that are described infra.

Additional work has focused upon the presentation of TRAs by the class of molecules known as human leukocyte antigens, or "HLAs". This work has resulted in several unexpected discoveries regarding the field. Specifically in U.S. patent application Ser. No. 938,334, now U.S. Pat. No. 5,405,940 the disclosure of which is incorporated by reference, nonapeptides are taught which are presented by the HLA-A1 molecule. The reference teaches that given the known specificity of particular peptides for particular HLA molecules, one might expect that a particular peptide will bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. patent application Ser. No. 008,446, filed Jan. 22, 1993 now abandoned and incorporated by reference, the fact that the MAGE-1 expression product is processed to a second TRA is disclosed. This second TRA is presented by HLA-C-clone-10 molecules. The disclosure shows that a given TRAP can yield a plurality of TRAs.

In U.S. Pat. No. 5,487,974 and incorporated by reference herein, tyrosinase is described as a tumor rejection antigen precursor. This reference discloses that a molecule which is produced by some normal cells (e.g., melanocytes), is processed in tumor cells to yield a tumor rejection antigen that is presented by HLA-A2 molecules.

U.S. patent application Ser. No. 190,411, filed Feb. 1, 1994, issued as U.S. Pat. No. 5,541,104, and incorporated by reference teaches the manufacture and use of a recombinant form of a MAGE tumor rejection antigen precursor, i.e., MAGE-1. The reference describes how MAGE-1 recombinant protein was made in *E. coli* host cells, purified, and then used as an immunogen to generate monoclonal antibodies specific for MAGE-1. Various uses of the monoclonal antibodies are also disclosed. Also, see Chen et al., Proc. Natl. Acad. Sci. USA 91:1004–1008 (1994); Chen et al., Proc. Natl. Acad. Sci. USA 92: 8125–8129 (1995), both of which are incorporated by reference, which teach, in detail, the manufacture and use of the recombinant MAGE-1 proteins and the monoclonal antibodies specific for MAGE-1.

An example of another tumor rejection antigen precursor is Melan-A, described by Coulie et al., J. Exp. Med. 180:35–42 (1994), incorporated by reference. The Melan-A TRAP is also described in U.S. patent application Ser. No. 08/032,978, filed on Mar. 18, 1993, issued as U.S. Pat. No. 5,620,886 and incorporated by reference herein. Also, see PCT Application PCT/US94/02487, which published on Sep. 29, 1994 as WO94/21126, and is also incorporated by reference herein. Kawakami et al, Proc. Natl. Acad. Sci. USA 91: 3515–3519 (1994), independently cloned the same gene and refer to it as MART-1.

The studies by Coulie et al and Kawakami et al suggest that Melan-A encodes a melanocyte differentiation antigen, which is expressed in normal melanocytes in the skin, retina, and cultured melanocytes, but not in other normal tissues examined.

The fact that the tumor rejection antigen precursors are expressed selectively, i.e., in cancerous cells and only in a very limited number of normal cells, renders them an ideal target for diagnosis of conditions such as cancer. Further, they can serve as targets for therapeutic treatments of disorders, such as cancer. Both diagnostic and therapeutic methods are features of the invention, as will now be discussed.

Monoclonal antibodies ("mAbs" hereafter), are well known as reagents which are extremely useful, both diagnostically and therapeutically. Their exquisite specificity permits the artisan to target a molecule of interest, and identify it, inactivate it, or interfere in some way with its normal properties and functions. While the techniques underlying the manufacture of monoclonal antibodies have improved greatly since the first reports, in 1975, much work still remains to be done. Key to development of any monoclonal antibody is availability of sufficient quantities of an immunogenic protein, where the protein is sufficiently pure to guarantee some degree of success in the protocols by which the mAbs are made. In the case of the tumor rejection antigen precursors, securing the necessary proteins is somewhat difficult. One reason for the difficulty is the nature of tumor rejection antigen precursors themselves. While these molecules are expressed, intracellularly, as full-sized proteins, they are processed to smaller nona-, deca- and undecapeptides. Thus, while genes encoding the full sized TRAPs have been isolated, applicants are unaware of any reports of success on isolating naturally occurring, or wild type TRAPs.

The isolation of nucleic acid molecules encoding TRAPs, such as Melan-A, might at first suggest a relatively simple way to produce sufficient amounts of the desired proteins. In practice, however, recombinant production of protein is far from routine. Even assuming one finds a useful model (promoter, vector, host cell, etc.), there is no guarantee that the resulting protein will be identical to the wild type molecule. For example, when Chen et al., Proc. Natl. Acad. Sci. 91:1004–1008 (1994), and Chen et al., Proc. Natl. Acad. Sci. USA 92:8125–8129 (1995) successfully cloned the gene for MAGE-1 into *E. coli*, the resulting protein was identifiable as MAGE-1. Its apparent molecular weight, however was not even close to being identical to the molecule one would predict from the isolated cDNA for MAGE-1. Despite this superficial discrepancy, the recombinant form of the molecule did act as an immunogen, provoking production of mAbs which bound to both the recombinant and the wild type form of MAGE-1.

The inventors have now successfully cloned the Melan-A gene into a host cell and produced a recombinant form of the Melan-A protein. The recombinant Melan-A is identifiable as a TRAP, but differs significantly from the molecule which one would predict from the isolated gene. Further, the invention relates to monoclonal antibodies which specifically bind to the TRAP Melan-A, the hybridomas which produce them, and various uses of the mAbs and the recombinant protein. Of particular interest is the fact that these mAbs are useful in immunohistochemical analysis.

These, and other features of the invention are elaborated upon in the disclosure which follows.

DETAILED DESCRIPTION OF PREFERRED EMBODIMENTS

EXAMPLE 1

As a first step, melanoma cell lines were tested to determine if they did, in fact, express Melan-A mRNA.

Ten melanoma cell lines, and forty four specimens of melanoma, were studied. Melan-A mRNA expression was determined using the well known reverse transcription polymerase chain reaction ("RT-PCR" hereafter), the details of which follow.

First, total RNA was removed from the cell lines or the melanoma samples, the latter having been snap frozen prior to the extraction. The removal was carried out using standard, well known techniques.

The total RNA was then reverse transcribed into cDNA, and then amplified via PCR (35 cycles, annealing temperature of 60° C.). The primers used in the PCR, i.e., 5'-primer:

5'-CACACAGGATCCGATGACGATGAC AAAATGCCAAGAGAAGATGCTCAC-3'  (SEQ ID NO: 1)

and

3'-primer:

5'-CACACAAAGCTTGTCTCGCTGGCTCTTAAGGTG-3'  (SEQ ID NO: 2)

were chosen based upon the published sequences of Melan-A and Mart-a, as per Coulie et al, J. Exp. Med. 180:35–42 (1994); et al, Proc. Natl. Acad. Sci. USA 91:2515–3519 (1994), both of which are incorporated by reference. The 5'-primer contains the N-terminus sequence of Melan-A, a BamHI cleavage site, and a sequence which encodes an enterokinase cleavage site. The 3'-primer contains the C-terminus, 3'-untranslated sequences of Melan-A, and a HindIII cleavage site for cloning. In each RT-PCR, a sample of 2 ug of total RNA was used. Full details of the RT-PCR protocol are presented in Chen et al, Proc. Natl. Acad. Sci. USA 91:1004–1008 (1994), which is incorporated by reference.

Table 1, which follows, presents the results obtained with the cell lines. Parallel experiments were carried out to determine presence of mRNA for tyrosinase, and these results are presented in Table 1 as well.

The results for the melanoma samples are not presented in tabular form; however, of the 44 samples tested, 39 were positive for Melan-A expression, four were negative, and one was equivocal.

Morphologically, no distinctions were found between samples which were positive and those which were negative for Melan-A mRNA expression.

The product of the RT-PCR was the expected 409 base pair product, from Melan-A mRNA positive cell lines. Presumptively, the full length message encodes a protein of 118 amino acids.

TABLE 1

Expression of tyrosinase and Melan-A mRNA in melanoma cell lines*

|  | Tyrosinase | Melan-A |
|---|---|---|
| MZ2-MML3.1 | − | − |
| MZ2-MEL2.2 | − | − |
| SK-MEL-13 | + | + |
| SK-MEL-19 | + | + |
| SK-MEL-23 | + | + |
| SK-MEL-28 | + | + |
| SK-MEL-30 | + | + |
| SK-MEL-31 | − | − |
| SK-MEL-33 | − | − |
| SK-MEL-187 | − | − |

*By RT-PCR analysis, using 2 μg total RNA for each assay. PCR primers for evaluating tyrosinase expression were previously described

EXAMPLE 2

As indicated, supra, the Melan-A primers used to amplify cDNA contained BamHI and HindIII cleavage sites. The amplified cDNA was digested with these endonucleases, using established procedures, and the resulting cDNA product was expression-cloned into the plasmid vector pQE9, and then used to transform *E. coli*. Recombinant protein production was then induced via IPTG, as the host plasmid contains the inducible lac operon. The protein was then purified by $Ni^{2+}$ ion affinity chromatography. Full details of the protocol which was used may be found in Chen et al., Proc. Natl. Acad. Sci. USA 91:1004–1008 (1994); Chen et al., Proc. Natl. Acad. Sci USA 92:8125–8129 (1995), both of which are incorporated by reference in their entirety.

The purified protein was then subjected to SDS-PAGE (a 4% stacking gel, and a 15% resolving gel), and it was found that the recombinant Melan-A protein had an apparent molecular weight, via SDS-PAGE, of about 23 kilodaltons. This is larger than the predicted molecular weight of primary translation product, which is about 13 kilodaltons.

EXAMPLE 3

Following purification of the recombinant Melan-A protein, monoclonal antibodies were prepared. BALB/C mice were immunized via five subcutaneous injections, at 2–3 week intervals. The immunizing formulation included 50 ug of recombinant protein in adjuvant. The first injection used Complete Freund's Adjuvant, and Incomplete Freund's Adjuvant was used thereafter. Spleen cells were taken from the immunized mice, and fused with mouse myeloma cell line SP2/0, to generate hybridomas.

Once hybridomas were generated, they were cloned, and their supernatants were screened against recombinant protein, using a standard solid phase ELISA on microtiter plates. The assay was in accordance with Dippold et al., Proc. Natl. Acad. Sci. USA 77: 6114–6118 (1980), incorporated by reference. A series of negative controls were also run, using recombinant MAGE-1 and human tyrosinase.

Ten hybridomas were found to produce monoclonal antibodies against Melan-A. These hybridomas are designated A9, A103, A154, A344, A355, A492, A528, A713, A753, A882. The ELISA titers for these clones ranged from 8,000 to 32,000.

EXAMPLE 4

A series of immunoblotting and immunoprecipitation experiments were then carried out. Cell lines SK-MEL-19, MZ2-MEL 2.2, and SK-MEL-187 were lysed with detergent NP-40 (Nonidet P40), in a buffer of 1% NP-40, 50 mM Tris-HCl, pH 8.0, 150 mM NaCl. The chemiluminiscent system of Chen et al., supra, was used. Each of the 10 positive hybridomas were tested, at 1:10 dilutions of hybridoma supernatant.

The immunoblotting showed positive results for SK-MEL-19 lysate, for each of the 10 hybridomas. No reactivity in any of the immunoblots was found for any of the hybridomas for either of MZ2-MEL 2.2, or SK-MEL-187. This is in accordance with the RT-PCR, discussed supra. Review of Table 1 will show that there was abundant Melan-A mRNA for SK-MEL-19, and none in either of MZ2-MEL 2.2 or SK-MEL-187.

An additional set of cell lines, i.e., SK-MEL-13, SK-MEL-23, SK-MEL-28, and Melan-A mRNA-negative cell line MZ2-MEL 3.1 were tested, in the same way. Hybridoma cell line A103 produced a monoclonal antibody which detected a protein doublet, at 20–22 kilodaltons in the three cell lines which had tested positive in the mRNA assay, but not Melan-A in mRNA negative line MZ2-MEL 3.1. The monoclonal antibody produced by hybridoma A355 detected this doublet, and also detected proteins having estimated molecular masses of 9, 15, 30, 35 and 42 kilodaltons. The remaining hybridomas all produced monoclonal antibodies which bound to the 20–22 kilodalton doublet, but none bound to other proteins.

EXAMPLE 5

In these experiments, cell lines SK-MEL-19, SK-MEL-13 and SK-MEL-187 were metabolically labelled with $^{35}$S-methionine, using Trans $^{35}$S-label. Following the labelling, the cells were lysed in lysis buffer (0.01M Tris.HCl/0.15M NaCl/0.01M $MgCl_2$/0.5% NP-40/aprotinin (20 ug/ml)/2mM phenylmethylsulfonyl fluoride), and then immunoprecipitated with monoclonal antibodies produced by hybridoma cell line A103, in accordance with Rettig, et al., Cancer Res. 53: 3327–3335 (1993); Rettig et al., Int. J. Cancer 58:385–392 (1994), both of which are incorporated by reference.

As with the immunoblotting experiments of example 4, supra, a 20–22 kD species was identified in lysates of SK-MEL-19 and SK-MEL-13, but not in the Melan-A negative line, SK-MEL-187.

Due to the strong, and consistent nature of their immunoreactivity, the monoclonal antibodies produced by A103 and A355 were purified, identified as belonging to subclass IgG1, and used in the experiments which follow.

EXAMPLE 6

In these experiments, the monoclonal antibodies produced by A103 and A355 were used, in immunohistochemical analyses of melanoma cell lines SK-MEL-19 and MZ2-MEL 3.1, as well as in a number of melanoma and normal tissue samples.

The assays on the cell lines used an avidin-biotin-complex immunoperoxidase procedure, as described by Garin-Chesa et al., Am. J. Pathol. 139:275–286 (1991), incorporated by reference. Essentially, acetone fixed samples (100% acetone at 4° C. for 10 minutes) of the cell lines were contacted with one of the test monoclonal antibodies, followed by biotinylated anti-igG, and then a complex of avidin and horseradish peroxidase, followed by contact with the horseradish peroxidase substrate diaminobenzidine tetrahydrochloride. For tissue samples also fixed in acetone as described supra, the biotinylated antibodies were contacted with complexes of streptavidin and alkaline phosphatase, followed by a fuchsin substrate. The use of this system rather than the "classic" ABC system facilitates staining, because the red reaction product is easily distinguishable from the brown-black pigment in melanocytes of normal skin, and pigmented melanomas.

The immunocytochemical (i.e., immunohistochemical) staining of cell lines SK-MEL-19 and MZ2-MEL 3.1 correlated with expression of Melan-A mRNA. Specifically, there was strong cytoplasmic staining for SK-MEL-19, and not for MZ2-MEL 3.1.

Three normal skin specimens were tested and, in all cases, there was strong cytoplasmic staining of the melanocytes in the samples.

Additional samples of normal stomach, colon, lung, liver, spleen, kidney, testis, urinary bladder, breast, ovary, smooth muscle and adipose tissue were tested. All were negative.

Twenty-one melanoma specimens were analyzed, of which 17 had tested as Melan-A mRNA positive, three as negative, and one equivocal (see supra). Of the seventeen mRNA positive samples, 15 were positive in the cytoplasmic staining (greater than 80–90% of melanoma cells). One showed only rare, scattered positive results (less than 0.5%), with one being negative for staining with A103. All three mRNA negative samples were also negative for staining with the monoclonal antibody, with the single equivocal case showing a single, microscopic focus of positively stained tumor cells. The tests on A355 were identical to those for A103.

EXAMPLE 7

Since most pathological human tissues received for the diagnosis of cancer are routinely fixed in formalin, and embedded in paraffin, it would be extremely valuable if monoclonal antibodies were available which react, not only with fresh frozen tissue samples, but with tissue samples fixed as discussed herein.

In experiments not detailed herein, monoclonal antibody A103 was tested with formalin fixed tissues. The mAb was found to react strongly with, and only with, melanocytes. This pattern is identical to the results discussed herein on fresh tissues.

A set of experiments were then carried out, wherein frozen and paraffin embedded tissues were tested. Samples taken from seven different metastatic melanoma cases were examined. Six of these had tested positive for Melan-A mRNA expression, and one had tested negative.

When mAb A103 was used in immunohistochemical assays on these samples, the results correlated 100% with the Melan-A mRNA expression results.

The foregoing experiments describe the production of monoclonal antibodies which specifically bind to a tumor rejection antigen precursor TRAP. The studies show binding both to the "wild type" Melan-A molecule, and the recombinant form, but not any other TRAP. A particularly preferred species of Melan-A binding mAb, i.e., A103, has been deposited at the American Type Culture Collection 12301 Parklawn Drive, Rockville, Md. 20852 in accordance with the Budapest Treaty on March 7, 1996 under Accession Number HB 12059.

The invention thus relates to Melan-A specific monoclonal antibodies and the hybridomas which produce them. The mAbs were found to be useful in determining expression of Melan-A in cell lysates. Specifically, the mAbs can be added, e.g., in labelledform, bound to a solid phase, or otherwise treated to increase the sensitivity of Melan-A detection. Any of the standard types of immunoassays, including ELISAs, RIAs, competitive assays, agglutination assays, and all others are encompassed with respect to the way the mAbs can be used. The mAbs may be used in immunohistochemical assays, such as the assays discussed supra. It must be pointed out that this type of assay is of special value for determining normal and cancerous melanocytes when assaying tissue samples. A certain percentage of cancerous melanocytes do not express pigment, and the condition is referred to as amelanotic melanoma. These tumors, when presented as metastatic lesions, are especially difficult to diagnose as a result of the absence of pigment in the cancerous cells. The mAbs of the invention are useful in diagnosing this form of melanoma, as well as all others. The detection of Melan-A expression product is useful in diagnosing or monitoring the presence or progress of a cancer.

It is to be understood that "monoclonal antibody" as the term is used herein embraces not only the products of hybridomas, but also monoclonal antibodies produced via other well known methodologies. Such methodologies include, but are not limited to, e.g., the use of cells which have been "immortalized" by transfection with Epstein Barr Virus or other immortalizing agents. Also embraced are monoclonal antibodies produced via genetic engineering, such as by transformation of appropriate host prokaryotic or eukaryotic cells. Also covered are chimeric antibodies. These are well known in the art as antibodies which contain portions of antibodies from two or more species. For example, it is well known to produce chimeric antibodies which contain the CDR region of a murine monoclonal antibody, and the remaining portions of a human monoclonal antibody. Such chimeras are extremely useful, e.g., in a therapeutic context. It also embraces the well known binding fragments of antibodies, such as the Fab, $F(ab)_2$, Fv and other binding fragments. Also covered by the invention are oligomeric, and polymeric constructions, where a plurality of monoclonal antibodies of the recited specificity are complexed to each other.

The antibodies of the invention can clearly be used in diagnostic methods to identify Melan-A expression, whereby the monoclonal antibody is contacted to a sample to be assayed, and its binding is monitored. Such binding can be determined using any of the standard immunoassay protocols known to the artisan, including, but not being limited to, radioimmunoassays, enzyme linked immunosorbent assays, sandwich assays, competitive assays, chromophoric assays and so forth. Many of these assays require the use of a detectable label which is attached to the antibody, and any of the labels known to the art, including radioactive, chromophoric, and fluorophoric substrates, enzymes, magnetic particles, and metallic particles may be used. In carrying out the assays, the sample of interest may be, e.g., a tissue sample or body fluid sample. Further, the specificity of the mAb permits the artisan to use it in vivo diagnosis. Among the varieties of in vivo diagnosis which can be used, radioimaging may be mentioned as one, but is by no means the only alternative.

The isolated, recombinant Melan-A protein is also a feature of this invention. This molecule has a molecular weight of about 23 kDa as determined by SDS-PAGE, and is useful as an immunogen as are peptides derived therefrom. Preferably, these are used in combination with a suitable adjuvant such as Complete or Incomplete Freund's Adjuvant. Also a part of the invention is the isolated, wild type form of Melan-A, which has a molecular weight of about 23 kD based upon amino acid sequence, and is useful in the same ways as is the recombinant protein.

Also a feature of the invention are pharmaceutical compositions which contain the Melan-A tumor rejection antigen precursor and a pharmaceutically acceptable adjuvant. The Melan-A tumor rejection antigen precursor may be wild type or recombinant in form, such as the forms described herein. The adjuvant may be any of the standard, pharmaceutically acceptable adjuvants known to the art, which need not be recited here.

Also a feature of the invention is the use of the Melan-A tumor rejection antigen precursor in the manufacture of pharmaceuticals and/or medicaments for treatment of conditions such as melanoma.

Note that Melan-A tumor rejection antigen precursor may be replaced, in any of the recited objects, by Melan-A specific monoclonal antibodies, such as those disclosed therein. Both the mAbs and the TRAPs may be used diagnostically, in in vitro determinations of diseases or disease states, such as those listed supra.

Other features of the invention will be clear to the artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Hybridoma cell line ATCC HB 12059 which produces a monoclonal antibody that specifically binds to a target comprising at least one protein selected from the group consisting of a tumor rejection antigen precursor Melan-A and a recombinant minor rejection antigen precursor rMelan-A, said rMelan-A having a molecular weight of about 23 KDa as determined by SDS-PAGE.

2. A monoclonal antibody produced by the hybridon cell line ATCC HB 12059 of claim 1.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA
        ( A ) DESCRIPTION: SEQ ID NO:1

( x i ) SEQUENCE DESCRIPTION: SEQ ID NO:1:

```
CACACAGGAT CCGATGACGA TGACAAAATG CCAAGAGAAG ATGCTCAC      48
```

( 2 ) INFORMATION FOR SEQ ID NO: 2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA
        ( A ) DESCRIPTION: SEQ ID NO: 2

( x i ) SEQUENCE DESCRIPTION: SEQ ID NO: 2:

```
CACACAAAGC TTGTCTCGCT GGCTCTTAAG GTG 33
```